(12) United States Patent
Foley

(10) Patent No.: US 8,372,116 B2
(45) Date of Patent: Feb. 12, 2013

(54) SYSTEMS AND DEVICES FOR DYNAMIC STABILIZATION OF THE SPINE

(75) Inventor: Kevin T Foley, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 284 days.

(21) Appl. No.: 12/422,387

(22) Filed: Apr. 13, 2009

(65) Prior Publication Data

US 2010/0262192 A1 Oct. 14, 2010

(51) Int. Cl.
*A61B 17/70* (2006.01)

(52) U.S. Cl. ...................................... 606/247

(58) Field of Classification Search .................. 606/264, 606/246–249, 254–261, 263; 623/17.11–17.14
See application file for complete search history.

(56) References Cited

U.S. PATENT DOCUMENTS

| | | | |
|---|---|---|---|
| 5,375,823 A * | 12/1994 | Navas | 623/17.15 |
| 5,480,401 A | 1/1996 | Navas | |
| 6,610,091 B1 * | 8/2003 | Reiley | 623/17.11 |
| 6,884,241 B2 * | 4/2005 | Bertranou et al. | 606/261 |
| 7,175,622 B2 | 2/2007 | Farris | |
| 7,291,150 B2 | 11/2007 | Graf | |
| 7,815,664 B2 * | 10/2010 | Sherman et al. | 606/257 |
| 2003/0045875 A1 * | 3/2003 | Bertranou et al. | 606/61 |
| 2004/0049190 A1 | 3/2004 | Biedermann et al. | |
| 2004/0143264 A1 | 7/2004 | McAfee | |
| 2004/0225289 A1 | 11/2004 | Biedermann | |
| 2005/0113927 A1 | 5/2005 | Malek | |
| 2005/0261685 A1 * | 11/2005 | Fortin et al. | 606/61 |
| 2005/0288670 A1 * | 12/2005 | Panjabi et al. | 606/61 |
| 2006/0082987 A1 | 4/2006 | Dorsey et al. | |
| 2006/0113927 A1 | 6/2006 | Bondy et al. | |
| 2006/0149238 A1 * | 7/2006 | Sherman et al. | 606/61 |
| 2006/0149242 A1 * | 7/2006 | Kraus et al. | 606/61 |
| 2006/0229609 A1 * | 10/2006 | Wang | 606/61 |
| 2006/0264935 A1 * | 11/2006 | White | 606/61 |
| 2006/0264940 A1 | 11/2006 | Hartmann | |
| 2006/0265074 A1 * | 11/2006 | Krishna et al. | 623/17.15 |
| 2006/0293657 A1 | 12/2006 | Hartmann | |
| 2006/0293663 A1 | 12/2006 | Walkenhorst et al. | |
| 2007/0029362 A1 | 2/2007 | Caillaud et al. | |
| 2007/0049936 A1 | 3/2007 | Colleran et al. | |
| 2007/0049937 A1 * | 3/2007 | Matthis et al. | 606/61 |
| 2007/0078461 A1 | 4/2007 | Shluzas | |
| 2007/0100341 A1 | 5/2007 | Reglos et al. | |
| 2007/0123863 A1 * | 5/2007 | Winslow et al. | 606/61 |
| 2007/0161997 A1 | 7/2007 | Thramann et al. | |
| 2007/0233085 A1 | 10/2007 | Biedermann et al. | |
| 2007/0233091 A1 | 10/2007 | Naifeh et al. | |

(Continued)

OTHER PUBLICATIONS

Response to Office Action for U.S. Appl. No. 12/422,606, filed Jun. 23, 2011.

(Continued)

*Primary Examiner* — Ellen C Hammond
*Assistant Examiner* — Jacqueline Johanas

(57) ABSTRACT

A dynamic stabilization system for use with a spinal motion segment includes a first bone anchor assembly, a second bone anchor assembly, and a resilient element. The resilient element includes an end portion engageable with the first bone anchor assembly and a resilient portion engageable with the second bone anchor assembly. The resilient element provides resilient resistance when the first and second bone anchor assemblies are moved toward one another and provides no resistance and is separable from the second bone anchor assembly when the first and second bone anchor assemblies are moved away from one another.

16 Claims, 3 Drawing Sheets

U.S. PATENT DOCUMENTS

| | | |
|---|---|---|
| 2007/0270810 A1 | 11/2007 | Sanders |
| 2007/0270814 A1 | 11/2007 | Lim et al. |
| 2007/0270837 A1 | 11/2007 | Eckhardt et al. |
| 2007/0270838 A1 | 11/2007 | Bruneau et al. |
| 2007/0288009 A1 | 12/2007 | Brown et al. |
| 2007/0293862 A1 | 12/2007 | Jackson |
| 2008/0021459 A1 | 1/2008 | Lim |
| 2008/0039847 A1 | 2/2008 | Piper et al. |
| 2008/0065073 A1 | 3/2008 | Perriello et al. |
| 2008/0183213 A1 | 7/2008 | Veldman et al. |
| 2008/0234739 A1* | 9/2008 | Hudgins et al. ............... 606/255 |
| 2008/0275504 A1* | 11/2008 | Bonin et al. .................. 606/246 |
| 2008/0300630 A1* | 12/2008 | Bonnema et al. ............. 606/246 |
| 2009/0088799 A1* | 4/2009 | Yeh .............................. 606/246 |
| 2009/0228045 A1* | 9/2009 | Hayes et al. .................. 606/257 |
| 2010/0262187 A1* | 10/2010 | Marik et al. .................. 606/246 |
| 2010/0262191 A1* | 10/2010 | Marik et al. .................. 606/264 |

OTHER PUBLICATIONS

Response to Office Action for U.S. Appl. No. 12/422,367, filed Jun. 23, 2011.

* cited by examiner

SYSTEMS AND DEVICES FOR DYNAMIC STABILIZATION OF THE SPINE

BACKGROUND

Elongated connecting elements, such as rods, plates, tethers, wires, cables, and other devices have been implanted along the spinal column and connected between two or more anchors engaged between one or more spinal motion segments. Some connecting elements provide a rigid construct that resists movement of the spinal motion segment in response to spinal loading or movement of the spinal motion segment by the patient. Still other connecting elements are flexible to permit at least limited spinal motion while providing resistance to loading and motion of the spinal motion segment. Such flexible connecting elements can be considered to provide dynamic spinal stabilization since at least limited movement of the spinal motion segment is preserved after implantation of the connecting element.

SUMMARY

The present invention generally relates to systems, devices, and methods for dynamically stabilizing a spinal column motion segment including at least two vertebrae by engaging a resilient element between the two vertebrae. An exemplary resilient element includes an end portion and a resilient portion positioned between the two vertebrae.

In one aspect, a spinal stabilization system for dynamically stabilizing a first vertebral body with respect to a second vertebral body includes first and second anchor assemblies attachable to respective ones of the first and second vertebral bodies and a resilient element including an end portion and a resilient portion and having a length along a longitudinal axis sized for positioning between and engaging each of the first and second anchor assemblies when the first and second anchor assemblies are attached to the respective vertebral bodies. The resilient element further includes a tether extending from the end portion through the resilient portion along the longitudinal axis, such as within axial bores of each of the end portion and resilient portion.

In another aspect, a resilient element for stabilizing one vertebral body with respect to a second vertebral body in a dynamic spinal stabilization system includes an elongated body extending along a longitudinal axis that includes an end portion and a resilient portion attached to the end portion. The resilient element further includes a tether extending from the end portion through the resilient portion along the longitudinal axis, such as within axial bores of each of the end portion and resilient portion.

In yet another aspect, a method for dynamic stabilization of a spine includes implanting a first anchor assembly into a first substrate, the first anchor assembly having a connector, and a second anchor assembly into a second substrate, the second anchor assembly including an articulation surface. A resilient element having an end portion and a resilient portion is positioned such that the end portion is connectable to the connector of the first anchor assembly and the resilient portion is engageable with the articulation surface of the second anchor assembly when the first anchor assembly and the second anchor assembly are moved closer to each other. The end portion is connected to the connector of the first anchor assembly.

These and other aspects are described below.

DESCRIPTION OF THE ILLUSTRATED EMBODIMENTS

Figure 1:
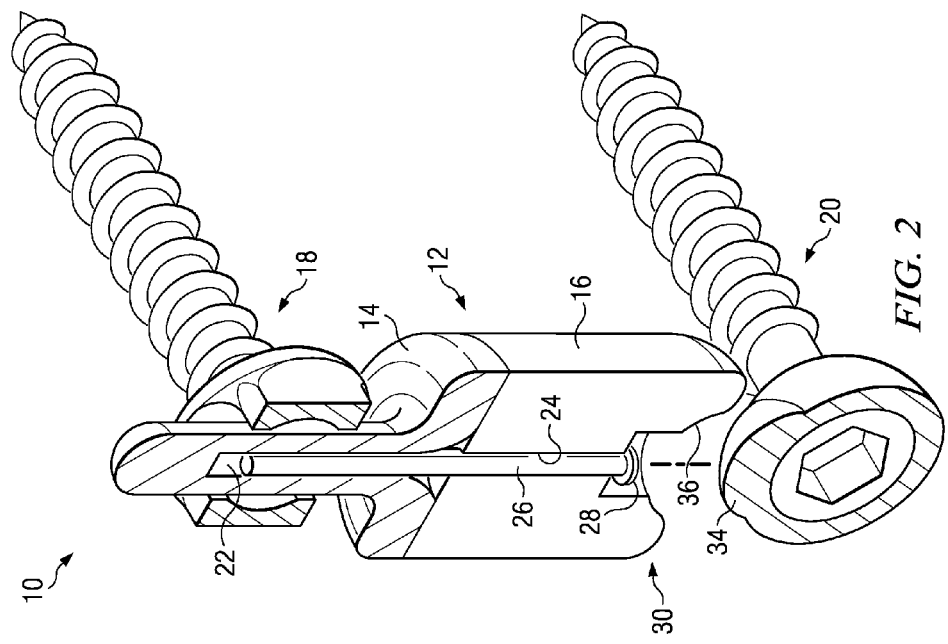
FIG. 1 is a perspective view partially in cross section of a dynamic stabilization system according to one embodiment of the present invention.

The present disclosure relates generally to the field of orthopedic surgery, and more particularly to systems and methods for stabilizing a spinal joint or spinal motion segment. For the purposes of promoting an understanding of the principles of the invention, reference will now be made to the embodiments illustrated in the drawings and specific language will be used to describe the same. It will nevertheless be understood that no limitation of the scope of the invention is thereby intended. Alterations and further modifications in the illustrated devices, as well as further applications of the principles of the invention as illustrated herein, are contemplated as would normally occur to one skilled in the art to which the invention relates.

Systems, devices, and methods for providing dynamic stabilization of one or more spinal motion segments are provided. The systems and devices include a resilient element positionable between at least two bone anchor assemblies that can be attached to at least two or more vertebral bodies of a spinal motion segment. The resilient element extends along a longitudinal axis and includes an end portion engageable to at least one of the anchor assemblies and a resilient portion attached to the end portion and engageable with an articulation surface of at least one of the bone anchor assemblies. The resilient member allows or enables movement of the vertebra to which the resilient element is attached and an adjacent vertebra to which the resilient element is not attached. The end portion can be attached to the resilient portion to provide a stabilization construct that is movable in response to at least spinal extension, spinal flexion and lateral bending of the spinal column. The resilient portion, or bumper assembly, defines multiple planes and locations of motion relative to the longitudinal axis of the resilient element while providing appropriate stiffness and resistance for spinal stabilization as the spinal motion segment deviates from the neutral position and the bone anchor assemblies move closer together.

The anchor assemblies discussed herein can be multi-axial or uni-axial in form, and can include an anchor member engageable to a vertebral body and a receiver, post or other device for receiving, connecting, or engaging the end portion or the resilient portion of the resilient element. The multi-axial anchor assemblies allow the anchor member to be positioned at various angles relative to the resilient element end portion of the anchor assembly. Uni-axial anchor assemblies provide a fixed positioning of the resilient element end portion to the anchor member. The anchor member of the anchor assemblies can take the form of a distal lower portion that is engageable to a vertebral body with the proximal resilient element connecting portion positioned adjacent the vertebral body.

The first and the second anchor assemblies can be the same or different. The first anchor assembly is configured to attach or connect the end portion. The second anchor assembly is configured to provide an articulation surface to cooperate with the resilient portion.

In one embodiment, the first and/or second anchor assembly is in the form of a bone screw with a threaded shaft and a proximal head that is pivotally attached thereto, such as a pedicle screw. In other embodiments, the anchor member can be in the form of a hook, staple, cable, tether, suture anchor, interbody fusion implant, artificial disc implant, bolt, or other structure engageable to bony tissue. The resilient element connecting portion can include a receiver with a U-shape, O-shape, or other shape that defines a passage that receives the respective end member of the connecting element therein, thereon, therethrough, or thereover, for example.

In one embodiment the second anchor assembly includes a head, post, or other structure to provide an articulation surface for engagement with the resilient portion of the resilient element. The second anchor assembly can be provided with a structure, such as a projection, bump, irregularity, or the like to engage a corresponding indentation or groove in the resilient portion.

FIG. 1 illustrates one embodiment of a bone anchor-based dynamic stabilization system 10 in accordance with the present invention. A resilient element 12 includes an end portion 14 and a resilient portion 16. The end portion 14 is attachable with a first bone anchor assembly 18. The resilient portion 16 is engageable with a second bone anchor assembly 20.

Resilient portion 16 and end portion 14 are attached or connected together. In one embodiment, end portion 14 includes a first passage 22 at least partially therethrough and resilient portion 16 includes a second passage 24 at least partially therethrough. A tether 26 is disposed within the passages 22, 24 to connect the end portion 14 and the resilient portion 16. In one embodiment, the tether 26 is provided with a head, ferrule, or stop member 28 disposed outside of the resilient portion 16 and configured to retain the resilient portion 16 against the end portion 14.

In one embodiment, tether 26 is crimped within the first passage 22 to retain tether 26 in position. Various embodiments of crimping and disposition of the tether 26 within the passages 22, 24 are described in U.S. Ser. No. 11/028,999, filed Jan. 4, 2005, which is incorporated herein by reference in its entirety.

Other embodiments include end portion 14 and resilient portion 16 attached or connected together by other mechanical connections, such as clips, straps, or the like, or by adhesive, glue, epoxy, or the like, or by chemical bonding.

Figure 2:
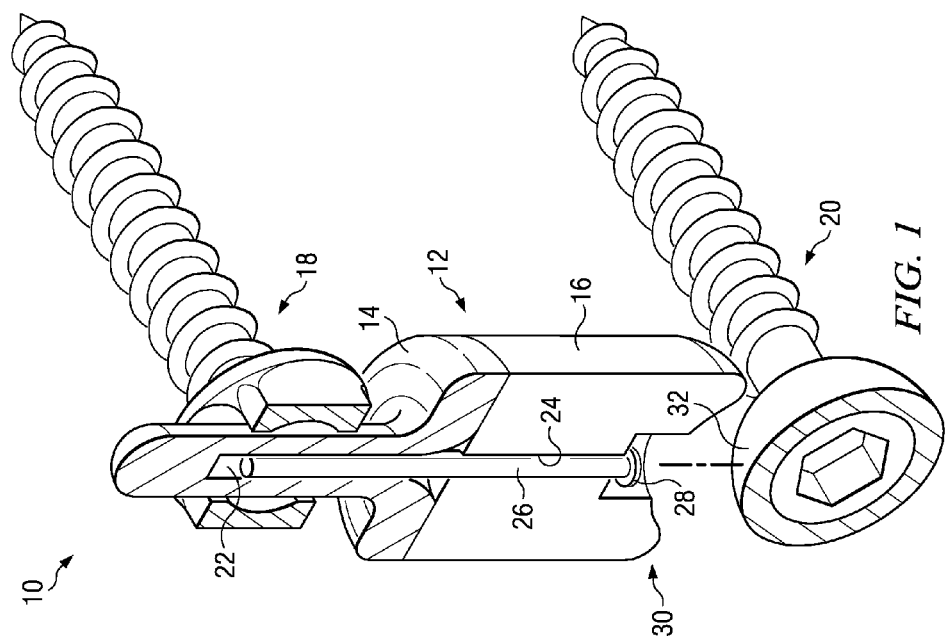
FIG. 2 is a perspective view partially in cross section of a dynamic stabilization system according to one embodiment of the present invention.

The cross-sectional shape of the resilient portion 16 may be circular, oval, or polygonal without departing from the spirit and scope of the invention. It is preferable, but not necessary, for the cross-sectional shape of the resilient portion 16 at the point of contact with the end portion 14 to match the cross-sectional shape of the end portion 14 at the point of contact with the resilient portion 16. The cross-sectional shape of the resilient portion 16 may vary along its length. The shape of the resilient portion 16 at its distal end 30 is selected to cooperate with an articulation surface 32 of the second bone anchor assembly 20. In one embodiment, this is the shape of a cup that cooperates with a corresponding shape of the articulating surface 32. FIG. 2 illustrates an embodiment in which the articulating surface 32 includes a projection 34 that fits into a cup-shaped indentation 36 on the distal end 30 of the resilient portion 16. Other embodiments include other shapes for the projection 34 and for the indentation 36 without departing from the spirit and scope of the invention. For example, the resilient portion 16 may be configured to partially surround a post-like structure, head, etc., on the second bone anchor assembly 20. In another embodiment, illustrated in FIG. 3, the distal end 30 is substantially flat.

Figure 4:
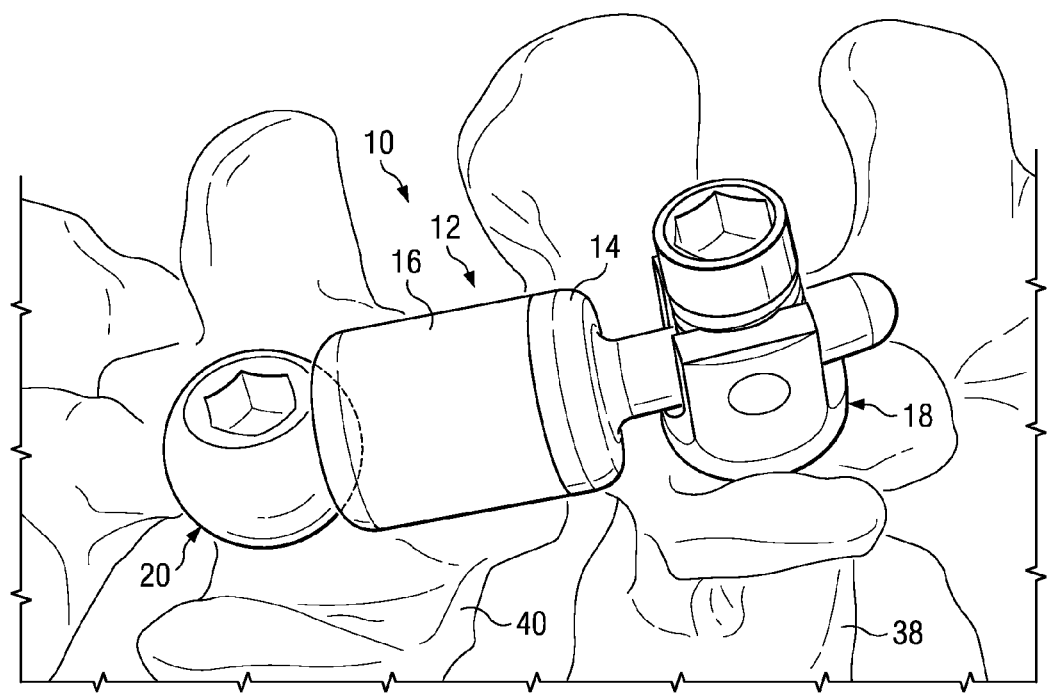
FIG. 4 is a perspective view of a dynamic stabilization system according to one embodiment of the present invention.

The first bone anchor assembly 18 is configured for engagement with a first substrate 38 and the second bone anchor assembly 20 is configured for engagement with a second substrate 40, as illustrated in FIG. 4. In one embodiment, the substrates 38, 40 are first and second human vertebrae. In other embodiments, the substrates 38, 40 include cadaveric vertebrae, sawbones, plastic, or other vertebral replicas, or other non-living substrates.

Figure 3:
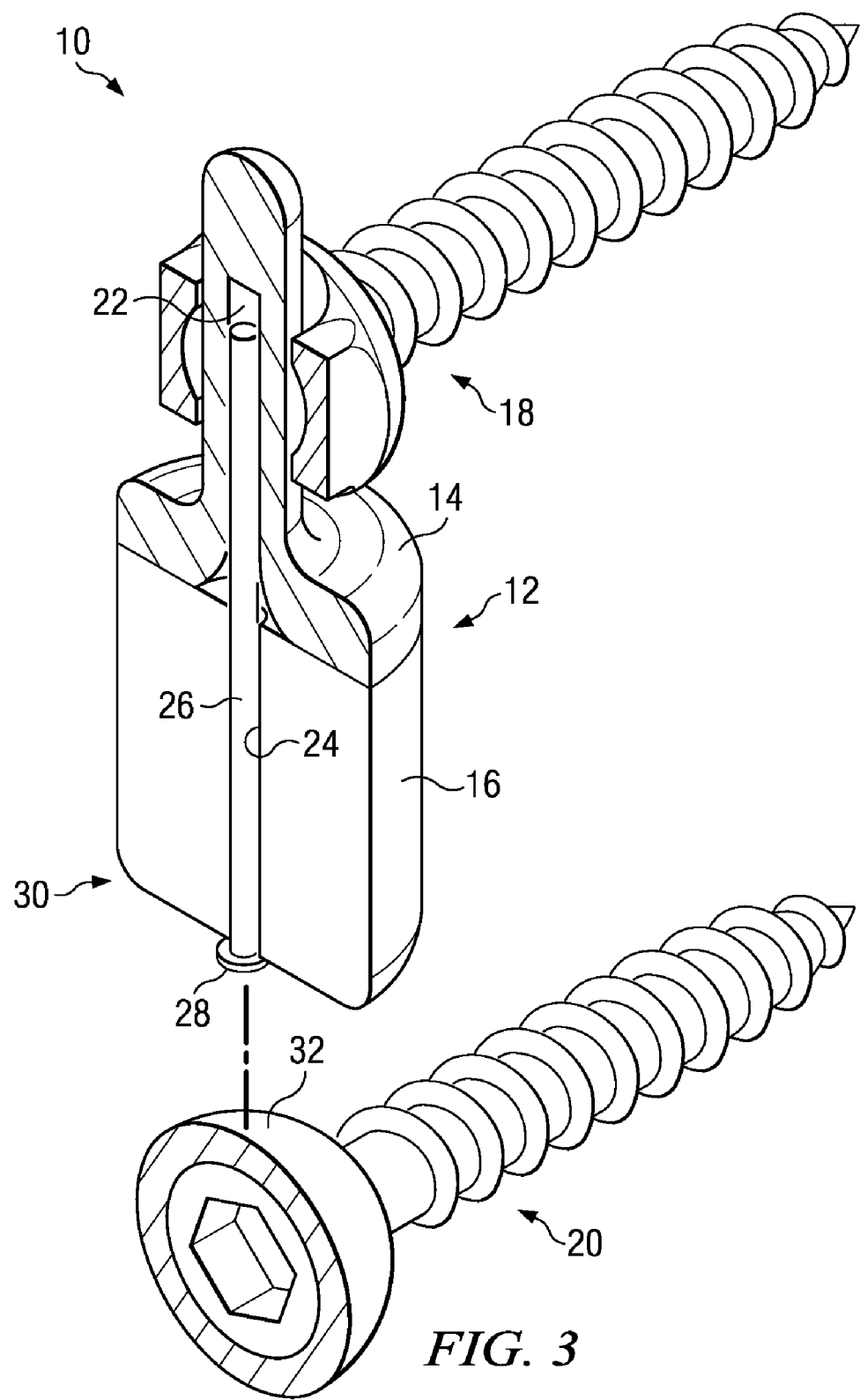
FIG. 3 is a perspective view partially in cross section of a dynamic stabilization system according to one embodiment of the present invention.

The articulation surface 32 of the second bone anchor assembly 20 may be attached to the bone anchor assembly 20 and not integral thereto. Or the articulation surface 32 of the second bone anchor assembly 20 may be integral thereto, as illustrated in FIGS. 1-3.

In operation, a user will implant the first bone anchor assembly 18 and the second bone anchor assembly 20 in a first substrate 38 and a second substrate 40. The user positions the resilient element 12 such that the end portion 14 is connectable to a connector of the first bone anchor assembly 18 and the resilient portion 16 is engageable with the articulation surface 32 of the second bone anchor assembly 20 when the first bone anchor assembly 18 and the second bone anchor assembly 20 are moved closer to each other. The end portion 14 is connected to the first bone anchor assembly. As noted above, in some embodiments the substrates 38, 40 are living and in some embodiments, the substrates 38, 40 are non-living. Implantation in living substrates, such as adjacent vertebrae, is to provide dynamic stabilization of the substrates. Implantation in non-living substrates could be for training, evaluation, development, or any other reason.

In one embodiment, the dynamic stabilization system 10 is implanted into a living patient using pedicle screws implanted into adjacent vertebrae via a posterior approach.

The articulation surface 32 and resilient portion 16 may be arranged so that when the substrates are in a neutral position, the articulation surface 32 and the resilient portion 16 abut. Or articulation surface 32 and resilient portion 16 may be arranged so that when the substrates are in a neutral position, the articulation surface 32 and the resilient portion 16 are separated and do not abut. A neutral position would be, for example, when a vertebral motion segment is at rest.

When the first bone anchor assembly 18 and the second bone anchor assembly 20 are moved toward each other, such as during extension of a spinal motion segment to which the system 10 is attached, the articulation surface 32 and the resilient portion 16 abut and engage. As the first bone anchor assembly 18 and the second bone anchor assembly 20 continue to be moved toward each other, the resilient portion 16 resists such movement and deflects to provide a dampening effect on the movement. As the first bone anchor assembly 18 and the second bone anchor assembly 20 are moved away from each other, the resilient portion 16 substantially returns to its original shape.

As the first bone anchor assembly 18 and the second bone anchor assembly 20 are moved away from each other, whether the articulation surface 32 and resilient portion 16 are in abutment or not, the system 10 provides no resistance to this movement. Thus, if the system 10 is attached to a vertebral motion segment, there is no resistance to flexion of the spine. In some embodiments, as the first bone anchor assembly 18 and the second bone anchor assembly 20 are moved away from each other, the resilient portion 16 is separated from and no longer abuts, or engages, the articulation surface 32 of the second bone anchor assembly 20. The resilient portion 16 is configured to be separable from and unattached to the articulation surface 32.

Although reference is made herein to use of the dynamic stabilization system 10 with adjacent vertebrae, or a spinal motion segment, some embodiments include use of the dynamic stabilization system 10 of the present invention across non-adjacent vertebrae, or multi-level, or across more than a single spinal motion segment. The size and scale of the components, the placement of the bone anchor assemblies, etc., will be different than that for a single motion segment with adjacent vertebrae. Likewise, the size, scale, placement, etc., for use with a single motion segment with adjacent vertebrae will be different depending on what specific motion segment and adjacent vertebrae are involved. For example, the size and spacing for the L4-L5 motion segment are different that the size and spacing for the L1-L2 motion segment and mat also vary from patient to patient or substrate to substrate. These size, scale, placement, etc., differences can be determined by one of ordinary skill in the art without undue experimentation.

The form, shape, and the material of construction of the end portion 14, the resilient portion 16, and the tether 26 can be selected based on criteria chosen by the user without departing from the spirit or scope of the invention. Some suitable materials are included in U.S. Ser. No. 11/028,999.

For example, the end portion 14 also may be made of metal, such as titanium. Examples of material that can be used for end portion 14 include cobalt-chromium alloys, titanium alloys, nickel titanium alloys, and/or stainless steel alloys, any member of the polyaryletherketone (PAEK) family such as polyetheretherketone (PEEK), carbon-reinforced PEEK, or polyetherketoneketone (PEKK); polysulfone; polyetherimide; polyimide; ultra-high molecular weight polyethylene (UHMWPE); and/or cross-linked UHMWPE.

Resilient portion 16 may be of any shape, such as cylindrical, conical, or prismatic, including rectangular, pentagonal, hexagonal, etc. prisms, and may be made from a resorbable material. The resilient portion 16 is, for example, flexible and resilient or elastic to permit motion of the spinal motion segment with which it is associated while providing a desired stabilization effect. The resilient portion 16 can be constructed such that it has a gradual or otherwise variable stiffness. Examples of material that can be used include any suitable biocompatible elastomer or polymer biomaterial, such as surgical latex, chloroprene, MIT's "biorubber" (glycerol and sebacic acid), polyethylene, polyester, polyurethane, urethane, polypropylene, polycarbonate urethane, silicone, or hydrogel, and combinations thereof. The resilient portion 16 can also be constructed in the form of a spring or any other shape exhibiting elastomeric properties from any suitable material. Examples of such material include cobalt-chromium alloys, titanium alloys, nickel titanium alloys, and/or stainless steel alloys.

The tether 26 may be flexible or inflexible, elastic, inelastic, or semi-elastic and of any suitable form, such as a wire, rope, cord, band, belt, suture, bar, cable, solid or hollow rod, mesh, fabric, or other suitable form and may be a metal cable, such as a titanium or titanium alloy cable. The tether 26 can be single strand, multiple strands, braided, or combinations thereof and constructed of any suitable material, preferably a biocompatible material. Examples of possible materials include but is not limited to woven or non-woven polymers, such as polyester, polyethylene, or any member of the polyaryletherketone (PAEK) family such as polyetheretherketone (PEEK), carbon-reinforced PEEK, or polyetherketoneketone (PEKK), polysulfone; polyetherimide, polyimide, ultra-high molecular weight polyethylene (UHMWPE), and/or cross-linked UHMWPE; superelastic metals, such as nitinol; shape memory alloy, such as nickel titanium; resorbable synthetic materials, such as suture material, metals, such as stainless steel and titanium; synthetic materials, allograft material; and bioelastomer material.

While the present invention has been illustrated by the above description of embodiments, and while the embodiments have been described in some detail, it is not the intention of the applicant to restrict or in any way limit the scope of the invention to such detail. Additional advantages and modifications will readily appear to those skilled in the art. Therefore, the invention in its broader aspects is not limited to the specific details, representative apparatus and methods, and illustrative examples shown and described. Accordingly, departures may be made from such details without departing from the spirit or scope of the applicant's general or inventive concept.

I claim:

1. A bone anchor-based spinal dynamic stabilization system, comprising:
   a. a first bone anchor assembly engageable with a first vertebra, the bone anchor assembly comprising an inner surface defining a U-shaped cavity;
   b. a second bone anchor assembly engageable with a second vertebra and having an articulation surface including an arcuate outer surface; and
   c. a resilient element defining a longitudinal axis, the resilient element comprising:
      i. an end portion defining a projection extending along the longitudinal axis and perpendicularly from a proximal end of the end portion configured for disposal in the U-shaped cavity to attach the resilient element to the first bone anchor assembly, and
      ii. a resilient portion including a cup-shaped inner cavity being disposed at a distal end of the resilient element such that the cup-shaped inner cavity has a center aligned with the longitudinal axis and is configured for disposal of and engagement with the arcuate outer surface of the articulation surface of the second bone anchor assembly, wherein the resilient portion is attached to the end portion and the resilient portion comprises a passage at least partially therethrough, the end portion comprises a passage at least partially therethrough, and a tether is disposed within the passage of the resilient portion and the passage of the end portion to attach the resilient portion to the end portion;
   wherein the resilient element is configured to be adjustable between the first vertebra and the second vertebra by movement of the projection within the U-shaped cavity such that the articulation surface is positioned relative the cup-shaped inner cavity when the first vertebra and the second vertebra are in a neutral position, and
   wherein the resilient element is configured to be separable from the second bone anchor assembly and is positionable between the first bone anchor assembly and the second bone anchor assembly to resiliently resist the movement of the first bone anchor assembly and the second bone anchor assembly towards each other.

2. The system of claim 1, wherein the resilient element is configured to provide no resistance to movement of the first bone anchor assembly and the second bone anchor assembly away from each other.

3. The system of claim 1, wherein the tether comprises a head disposed outside the resilient portion and configured to retain the resilient portion against the end portion.

4. The system of claim 1, wherein the articulation surface is attached to the second bone anchor assembly.

5. The system of claim 1, wherein the engagement of the resilient portion with the articulation surface of the second bone anchor assembly is by abutment.

6. The system of claim 5, wherein the resilient element comprises an indentation to accommodate the shape of the articulation surface.

7. The system of claim 1, wherein the bone anchor assemblies comprise pedicle screws.

8. The system of claim 1, wherein said resilient portion is connected to said end portion and is spaced from said first bone anchor assembly by said end portion.

9. The system of claim 1, wherein said resilient portion does not contact said first bone anchor assembly.

10. The system of claim 1, wherein said tether and said passages in said resilient portion and said end portion are each aligned along a transverse axis extending laterally between said first and second bone anchor assemblies.

11. A bone anchor-based spinal dynamic stabilization system, comprising:
   a. a first bone anchor assembly engageable with a first vertebra, the bone anchor assembly comprising an inner surface defining a U-shaped cavity:
   b. a second bone anchor assembly engageable with a second vertebra and having an articulation surface including an arcuate outer surface: and
   c. a resilient element defining a longitudinal axis, the resilient element comprising:
      i. an end portion defining a projection extending along the longitudinal axis and perpendicularly from a proximal end of the end portion configured for disposal in the U-shaped cavity to attach the resilient element to the first bone anchor assembly, and
      ii. a resilient portion including a cup-shaped inner cavity being disposed at a distal end of the resilient element such that the cup-shaped inner cavity has a center aligned with the longitudinal axis and is configured for disposal of and engagement with the arcuate outer surface of the articulation surface of the second bone anchor assembly;
   wherein the resilient element is configured to be adjustable between the first vertebra and the second vertebra by movement of the projection within the U-shaped cavity such that the articulation surface is positioned relative the cup-shaped inner cavity when the first vertebra and the second vertebra are in a neutral position, and
   wherein the resilient element is configured to be separable from the second bone anchor assembly and is positionable between the first bone anchor assembly and the second bone anchor assembly to resiliently resist the movement of the first bone anchor assembly and the second bone anchor assembly towards each other; and
   wherein the resilient portion is attached to the end portion:
   wherein the resilient portion comprises a passage at least partially therethrough, the end portion comprises a passage at least partially therethrough, and a tether is disposed within the passage of the resilient portion and the passage of the end portion to attach the resilient portion to the end portion: and
   wherein the tether is crimped within the passage of the end portion.

12. A resilient element defining a longitudinal axis and configured for use within a spinal dynamic stabilization system, comprising:
   a. an end portion for attachment to a first bone anchor assembly comprising an inner surface defining a U-shaped cavity, and
   b. a resilient portion including a cup-shaped inner cavity being disposed at a distal end of the resilient element such that the cup-shaped inner cavity has a center aligned with the longitudinal axis and is configured for disposal of and engagement with an arcuate outer surface of an articulation surface of a second bone anchor assembly, the resilient portion adjacent to the end portion, wherein the resilient portion is attached to the end portion and the resilient portion comprises a passage at least partially therethrough, the end portion comprises a passage at least partially therethrough, and a tether is disposed within the passage of the resilient portion and the passage of the end portion to attach the resilient portion to the end portion;
   c. wherein the resilient portion is configured to be unattached to the second bone anchor assembly;
   d. wherein the end portion defines a projection extending along the longitudinal axis and perpendicularly from a proximal end of the end portion configured for disposal in the U-shaped cavity to attach the resilient element to the first bone anchor assembly; and
   e. wherein the resilient element is configured to be adjustable between the first vertebra and the second vertebra by movement of the projection within the U-shaped cavity such that the articulation surface is positioned relative the cup-shaped inner cavity when the first vertebra and the second vertebra are in a neutral position.

13. The resilient element of claim 12, wherein the tether is crimped within the passage of the end portion.

14. The resilient element of claim 12, wherein the tether comprises a head disposed outside the resilient portion and configured to retain the resilient portion against the end portion.

15. The resilient element of claim 12, wherein said resilient portion is connected to said end portion and is spaced from said first bone anchor assembly by said end portion.

16. The resilient element of claim 12, wherein said resilient portion does not contact said first bone anchor assembly.

* * * * *